United States Patent
Shemi et al.

(10) Patent No.: US 10,006,030 B2
(45) Date of Patent: Jun. 26, 2018

(54) RNA INTERFERENCE COMPOSITIONS TARGETING HEAT SHOCK PROTEIN 90 AND METHODS OF USE THEREOF

(71) Applicant: SILENSEED LTD., Modi'in (IL)

(72) Inventors: Amotz Shemi, Herzliya (IL); Elina Zorde Khvalevsky, Jerusalem (IL)

(73) Assignee: SILENSEED LTD., Modi'In (IL)

( * ) Notice: Subject to any disclaimer, the term of this patent is extended or adjusted under 35 U.S.C. 154(b) by 0 days. days.

(21) Appl. No.: 15/326,044

(22) PCT Filed: Jul. 14, 2015

(86) PCT No.: PCT/IL2015/050724
§ 371 (c)(1),
(2) Date: Jan. 13, 2017

(87) PCT Pub. No.: WO2016/009428
PCT Pub. Date: Jan. 21, 2016

(65) Prior Publication Data
US 2017/0283803 A1   Oct. 5, 2017

Related U.S. Application Data

(60) Provisional application No. 62/023,982, filed on Jul. 14, 2014.

(51) Int. Cl.
*C12N 15/11* (2006.01)
*C12N 15/113* (2010.01)
*A61K 31/713* (2006.01)
*A61K 47/34* (2017.01)
*A61K 9/00* (2006.01)
*A61K 47/26* (2006.01)

(52) U.S. Cl.
CPC ........ *C12N 15/1135* (2013.01); *A61K 9/0024* (2013.01); *A61K 31/713* (2013.01); *A61K 47/26* (2013.01); *A61K 47/34* (2013.01); *C12N 2310/14* (2013.01); *C12N 2310/344* (2013.01); *C12N 2310/351* (2013.01); *C12N 2320/32* (2013.01)

(58) Field of Classification Search
CPC ........ A61K 9/0019; A61K 2039/55555; C12N 15/113; C12N 2310/14
See application file for complete search history.

(56) References Cited

U.S. PATENT DOCUMENTS

2011/0195123 A1   8/2011  Shemi

FOREIGN PATENT DOCUMENTS

WO   2010086849   8/2010

OTHER PUBLICATIONS

Mehta, Adi, et at. A novel therapeutic strategy for the treatment of glioma combining chemical and molecular targeting of hsp90a. Cancers, 2011, 3: 4228-4244.
Mehta, Adi, et al. Can RNAi-mediated hsp90a knockdown in combination with 17-AAG be a therapy for glioma?. FEBS open bio, 2013,3: 271-278.
Schoof, Nils, et at.HSP90 is essential for Jak-STAT signaling in classical Hodgkins lymphoma cells. Cell Commun Signal, 2009, 7:17.
Isaacs, Jennifer S.; Xu, Wanping; Neckers, Len. Heat shock protein 90 as a molecular target for cancer therapeutics. Cancer cell, 2003,3: 213-217.

*Primary Examiner* — Dana H Shin
(74) *Attorney, Agent, or Firm* — JMB Davis Ben-David

(57) ABSTRACT

This disclosure relates to RNA interference (RNAi) compositions that target expression of heat shock protein 90 (HSP90) in a subject. Polymeric delivery devices for providing the RNAi compositions are also described, as are methods of treating cancer using the described RNAi compositions.

5 Claims, 4 Drawing Sheets

RNA INTERFERENCE COMPOSITIONS TARGETING HEAT SHOCK PROTEIN 90 AND METHODS OF USE THEREOF

CROSS REFERENCE TO RELATED APPLICATIONS

This is the U.S. National Stage of International Application No. PCT/IL2015/050724 filed Jul. 14, 2015, which was published in English under PCT Article 21(2), and which in turn claims the benefit of U.S. Provisional Patent Application No. 62/023,982, filed Jul. 14, 2014.

FIELD

This disclosure relates to RNA interference (RNAi) compositions that target expression of heat shock protein 90 (HSP90) in a subject. Polymeric delivery devices for providing the RNAi compositions are also described, as are methods of treating cancer using the described RNAi compositions.

BACKGROUND

Heat shock proteins (HSPs) are a group of proteins induced by elevated temperatures or other stress. The most prominent HSPs are a class of functionally-related proteins involved in maintenance and remodelling of protein three-dimensional structure. Heat shock protein 90 (HSP90) is an ATP-dependent molecular chaperone that plays a central role in regulating the correct folding, stability, and function of numerous "client proteins," including human epidermal growth factor receptor 2 (HER2), BRAF, mutant EGFR, EML4-ALK, Bcr-Abl, Raf-1, and ABL, which are required for cancer cell survival. HPS 90 also is a known chaperone of AR (androgen receptor). Elevated, abnormal levels of HSP90 have been observed in human prostatic carcinoma (Palmieri et al 2014). It has also been reported that many oncogenic proteins essential for cancer transformation are chaperoned by the Hsp90 complex, and some of these client proteins have been discovered by using Hsp90 inhibitors, such as geldanamycin and radicicol.

In vitro studies show that inhibiting the HSP90 chaperone destabilizes macrophage migration inhibitory factor, and thereby inhibits breast tumor progression (Schultz et al 2012). Ex-vivo and in vitro studies of Hsp90 Inhibitors NVP-AUY922 and NVP-HSP990 were evaluated in the prostate cancer cell lines PC-3, LNCaP, and VCaP, and in an ex vivo culture model of human prostate cancer (Centenera et al 2012).

Due to its effect on a wide range of client proteins required for malignancy survival, HSP90 presents a potentially significant target for cancer treatment. Accordingly, a need exists for HSP90 targeting agents.

SUMMARY

Provided herein are RNAi (RNA interference) agents for treating a patient having a cancer in which cells of the cancer are expressing heat shock protein 90 (HSP90). The RNAi agent includes a sense strand and an antisense strand, wherein the RNAi agent targets an HSP90 mRNA transcript sequence which contains a sequence which in preferred embodiments is selected from the group consisting of SEQ ID Nos 1-3.

Also provided herein are drug delivery devices (DDD), which include a polymeric matrix, such as a biodegradable polymeric matrix; and at least one of the RNAi agents described herein, wherein the RNAi agent is incorporated within the biodegradable polymeric matrix. In addition to the RNAi agents described herein, additional RNAi agents and non-RNAi agents can be incorporated into the DDDs.

Further provided herein are methods for treating a cancer expressing HSP90 in a subject by administering the RNAi agent of claim 1 to the subject, thereby treating the cancer.

The foregoing and other objects, features, and advantages will become more apparent from the following detailed description, which proceeds with reference to the accompanying figures.

BRIEF DESCRIPTION OF THE DESCRIBED SEQUENCES

Figure 1:
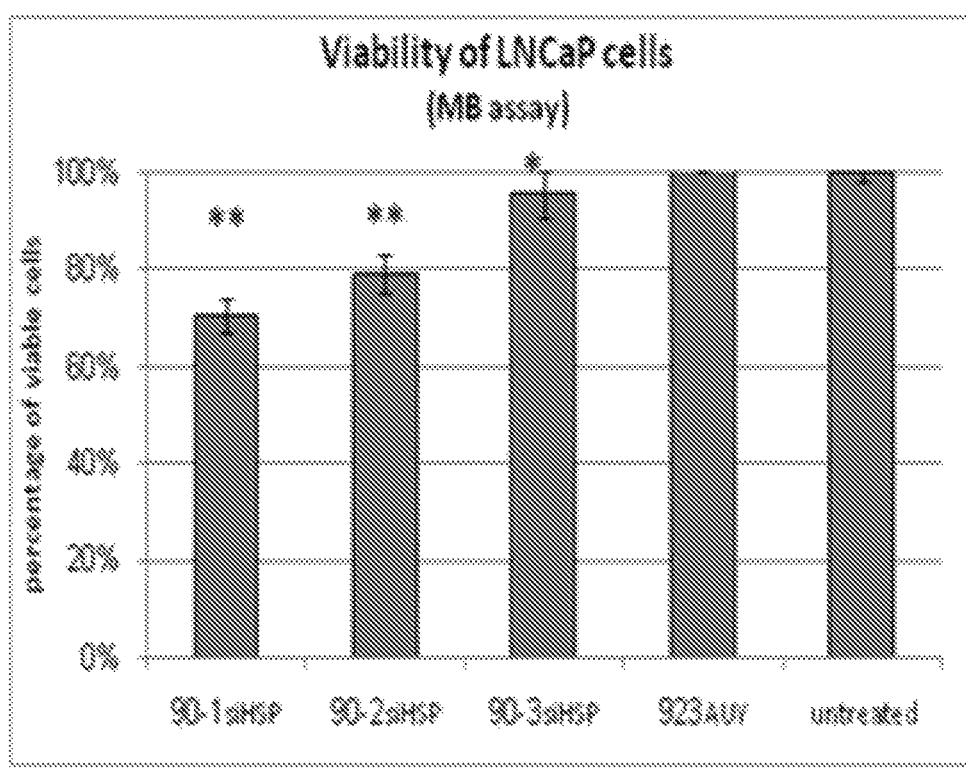
FIG. 1 shows a comparison of the in vitro effects of transfected siRNA targeting HSP90 and the HSP90 inhibitor AUY922 on cell viability as determined by methylene blue staining. The results shown are the percentage of untreated cells ** indicates p<0.001; * indicates p<0.05.

The nucleic and sequences provided herewith are shown using standard letter abbreviations for nucleotide bases as defined in 37 C.F.R. 1.822. Only one strand of each nucleic acid sequence is shown, but the complementary strand is understood as included by any reference to the displayed strand. The Sequence Listing is submitted as an ASCII text file named 2142_9_2.txt, created Jul. 13, 2015, about 3.5 KB, which is incorporated by reference herein. In the accompanying sequence listing:

SEQ ID NO: 1 is the HSP90 mRNA target sequence termed herein HSP1-1.

SEQ ID NO: 2 is the HSP90 mRNA target sequence termed herein HSP1-2.

SEQ ID NO: 3 is the HSP90 mRNA target sequence termed herein HSP1-3.

SEQ ID NO: 4 is the sense strand of a siRNA targeting HSP1-1.

SEQ ID NO: 5 is the sense strand of a siRNA targeting HSP1-2.

SEQ ID NO: 6 is the sense strand of a siRNA targeting HSP1-3.

SEQ ID NO: 7 is the sense strand of a 2'-o-methyl-modified siRNA targeting HSP1-1.

SEQ ID NO: 8 is the anti-sense strand of a siRNA targeting HSP1-1.

SEQ ID NO: 9 is the anti-sense strand of a siRNA targeting HSP1-2.

SEQ ID NO: 10 is the anti-sense strand of a siRNA targeting HSP1-3.

SEQ ID NO: 11 is the cell penetrating peptide Tat.

SEQ ID NO: 12 is the cell penetrating peptide MPG.

SEQ ID NO: 13 is the cell penetrating peptide Pep-1.

DETAILED DESCRIPTION

I. Abbreviations

AR Androgen receptor
HSP-90 Heat shock protein 90
LODER Local Drug EluteR
PLA Poly lactic acid
PGA Poly glycolic acid
PLGA Poly(lactic-co-glycolic acid)
RNAi RNA interference
siRNA Small interfering RNA

II. Terms

Unless otherwise noted, technical terms are used according to conventional usage. Definitions of common terms in molecular biology can be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

In case of conflict, the present specification, including explanations of terms, will control. In addition, all the materials, methods, and examples are illustrative and not intended to be limiting.

Administration: The introduction of a composition into a subject by a chosen route. Administration of an active compound or composition can be by any route known to one of skill in the art. Administration can be local or systemic. Examples of local administration include, but are not limited to, topical administration, intratumoral administration, subcutaneous administration, intramuscular administration, intrathecal administration, intra-ocular administration, topical ophthalmic administration, or administration to the nasal mucosa or lungs by inhalational administration. In addition, local administration includes routes of administration typically used for systemic administration, for example by directing intravascular administration to the arterial supply for a particular organ. Thus, in particular embodiments, local administration includes intra-arterial administration and intravenous administration when such administration is targeted to the vasculature supplying a particular organ. Local administration also includes the incorporation of active compounds and agents into implantable devices or constructs (such as the drug delivery devices described herein), which release the active agents and compounds over extended time intervals for sustained treatment effects. An implantable device is "implanted" by any means known to the art of insertion into the tissue or tissue environment that is the aim of a given treatment.

Systemic administration includes any route of administration designed to distribute an active compound or composition widely throughout the body via the circulatory system. Thus, systemic administration includes, but is not limited to intra-arterial and intravenous administration. Systemic administration also includes, but is not limited to, topical administration, subcutaneous administration, intramuscular administration, or administration by inhalation, when such administration is directed at absorption and distribution throughout the body by the circulatory system.

Altered expression: Expression of a biological molecule (for example, mRNA or protein) in a subject or biological sample from a subject that deviates from expression if the same biological molecule in a subject or biological sample from a subject having normal or unaltered characteristics for the biological condition associated with the molecule. Normal expression can be found in a control, a standard for a population, etc. Altered expression of a biological molecule may be associated with a disease such as a cancer. The term associated with includes an increased risk of developing the disease as well as the disease itself. Expression may be altered in such a manner as to be increased or decreased. The directed alteration in expression of mRNA or protein may be associated with therapeutic benefits.

Antisense inhibitor: Refers to an oligomeric compound that is at least partially complementary to the region of a target nucleic acid molecule to which it hybridizes. As used herein, an antisense inhibitor (also referred to as an "antisense compound") that is "specific for" a target nucleic acid molecule is one which specifically hybridizes with and modulates expression of the target nucleic acid molecule. As used herein, a "target" nucleic acid is a nucleic acid molecule to which an antisense compound is designed to specifically hybridize and modulate expression. Nonlimiting examples of antisense compounds include primers, probes, antisense oligonucleotides, siRNAs, miRNAs, shRNAs and ribozymes. As such, these compounds can be introduced as single-stranded, double-stranded, circular, branched or hairpin compounds and can contain structural elements such as internal or terminal bulges or loops. Double-stranded antisense compounds can be two strands hybridized to form double-stranded compounds or a single strand with sufficient self complementarity to allow for hybridization and formation of a fully or partially double-stranded compound.

Cancer: The product of neoplasia is a neoplasm (a tumor or cancer), which is an abnormal growth of tissue that results from excessive cell division. Neoplasia is one example of a proliferative disorder. A "cancer cell" is a cell that is neoplastic, for example a cell or cell line isolated from a tumor.

Examples of solid tumors, such as sarcomas and carcinomas, include fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers (such as small cell lung carcinoma and non-small cell lung carcinoma), ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, melanoma, and CNS tumors (such as a glioma, astrocytoma, medulloblastoma, craniopharyogioma, ependymoma, pinealoma, hemangioblastoma, acoustic neuroma, oligodendroglioma, menangioma, neuroblastoma and retinoblastoma).

Examples of hematological tumors include leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

Chemotherapeutic agent: An anti-cancer agent with therapeutic usefulness in the treatment of diseases characterized by abnormal cell growth or hyperplasia. Such diseases include cancer, autoimmune disease as well as diseases characterized by hyperplastic growth such as psoriasis. One of skill in the art can readily identify a chemotherapeutic agent (for instance, see Slapak and Kufe, *Principles of Cancer Therapy*, Chapter 86 in *Harrison's Principles of Internal Medicine,* 14th edition; Perry et al., *Chemotherapy*, Ch. 17 in Abeloff, *Clinical Oncology* $2^{nd}$ ed., © 2000 Churchill Livingstone, Inc; Baltzer L, Berkery R (eds): *Oncology Pocket Guide to Chemotherapy,* 2nd ed. St. Louis, Mosby-Year Book, 1995; Fischer D S, Knobf M F, Durivage H J (eds): *The Cancer Chemotherapy Handbook,* 4th ed. St. Louis, Mosby-Year Book, 1993). Examples of chemotherapeutic agents include ICL-inducing agents, such as melphalan (Alkeran™), cyclophosphamide (Cytoxan™), cis-platin (Platinol™) and busulfan (Busilvex™, Myleran™).

Drug Delivery Device (DDD): Device by which a therapeutic agent is provided to a subject. Non-limiting examples of DDDs include drug-eluting implants and stents. The LODER implant, is described herein for use with an RNAi agent, and is an illustrative DDD.

Injectable composition: A pharmaceutically acceptable fluid composition comprising at least one active ingredient, for example, a nucleic acid, including an RNAi agent, a peptide, or an antibody. The active ingredient is usually dissolved or suspended in a physiologically acceptable carrier, and the composition can additionally comprise minor amounts of one or more non-toxic auxiliary substances, such as emulsifying agents, preservatives, pH buffering agents and the like. Such injectable compositions that are useful for use with the compositions of this disclosure are conventional; appropriate formulations are well known in the art.

Local Drug EluteR (LODER): Millimeter scale drug delivery insertable device (DDD) or implant, composed of a polymer into which a given drug is incorporated. The drug, such as an RNAi agent, is released into the surrounding environment. In addition to the polymer and a drug, LODER can contain agents which alter (modify) the hydrophobicity and/or pH associated with LODER manufacturing and/or internal environment in-vivo.

Neoplasia, malignancy, cancer and tumor: A neoplasm is an abnormal growth of tissue or cells that results from excessive cell division. Neoplastic growth can produce a tumor. The amount of a tumor in an individual is the "tumor burden" which can be measured as the number, volume, or weight of the tumor. A tumor that does not metastasize is referred to as "benign." A tumor that invades the surrounding tissue and/or can metastasize is referred to as "malignant." Malignant tumors are also referred to as "cancer."

Pharmaceutical agent: A chemical compound or composition capable of inducing a desired therapeutic or prophylactic effect when properly administered to a subject or a cell. Incubating includes exposing a target to an agent for a sufficient period of time for the agent to interact with a cell. Contacting includes incubating an agent in solid or in liquid form with a cell, such as contacting a tumor with the described siRNA in suspension or as incorporated into a drug delivery device.

Preventing or treating a disease: Preventing a disease refers to inhibiting the development of a disease, for example inhibiting the development of myocardial infarction in a person who has coronary artery disease or inhibiting the progression or metastasis of a tumor in a subject with a neoplasm. Treatment refers to a therapeutic intervention that ameliorates a sign or symptom of a disease or pathological condition after it has begun to develop. In particular examples, treatment of a cancer can include inhibition of progression and/or prevention of a reoccurrence of the disease.

Radiation Therapy (Radiotherapy): The treatment of disease (e.g., cancer or another hyperproliferative disease or condition) by exposure of a subject or their tissue to a radioactive substance. Radiation therapy is the medical use of ionizing radiation as part of cancer treatment to control malignant cells. Radiotherapy may be used for curative or adjuvant cancer treatment. It is used as palliative treatment where cure is not possible and the aim is for local disease control or symptomatic relief.

RNA interference (RNA silencing; RNAi): A gene-silencing mechanism whereby specific molecules, such as a double-stranded RNA (dsRNA), trigger the degradation of homologous mRNA (also called target RNA). Double-stranded RNA can be or is processed into small interfering RNAs (siRNA), which serve as a guide for cleavage of the homologous mRNA in the RNA-induced silencing complex (RISC). The remnants of the target RNA may then also act as siRNA; thus resulting in a cascade effect. An RNAi agent is any nucleic acid that can either serve directly as siRNA, be processed into siRNA, or produce siRNA, for example DNA that is transcribed to produce RNA that in turn processed into siRNA.

Sense/anti-sense strand: The strand of dsDNA that containing the RNA transcript sequence (read from 5' to 3' direction) is the sense strand, and is also known as the "forward" strand. The opposite, reverse-complementary strand, which is used as the template for cellular RNA polymerase, is the antisense strand, and is also known as the "reverse" strand. Likewise in a dsRNA molecule, the "sense" strand corresponds to the target gene coding sequence, and with the antisense strand, its reverse complement.

Subject: Living multi-cellular organisms, including vertebrate organisms, a category that includes both human and non-human mammals.

Subject susceptible to a disease or condition: A subject capable of, prone to, or predisposed to developing a disease or condition. It is understood that a subject already having or showing symptoms of a disease or condition is considered "susceptible" since they have already developed it.

Target sequence: A target sequence is a portion of ssDNA, dsDNA, or RNA that, upon hybridization to a therapeutically effective oligonucleotide, results in the inhibition of expression of the target.

Therapeutically effective amount: A quantity of compound sufficient to achieve a desired effect in a subject being treated. An effective amount of a compound may be administered in a single dose, or in several doses, for example daily, during a course of treatment. However, the effective amount will be dependent on the compound applied, the subject being treated, the severity and type of the affliction, and the manner of administration of the compound.

Tumor bed: The tissue surrounding a solid tumor.

III. Overview of Several Embodiments

Provided herein are RNAi (RNA interference) agents for treating a patient having a cancer in which cells of the cancer are expressing heat shock protein 90 (HSP90). The RNAi agent includes a sense strand and an antisense strand, wherein the RNAi agent targets an HSP90 mRNA transcript sequence which contains a sequence which in some embodiments is selected from the group consisting of SEQ ID Nos 1-3.

In particular embodiments, the RNAi agents also include a dTdT at the 3'-end of at least one of the sense and antisense strands.

In some embodiments, the sequence of the sense strand contains a sequence selected from the group consisting of SEQ ID Nos 4-6; and in some embodiments, the sequence of the antisense strand contains a sequence selected from the group consisting of SEQ ID Nos 8-10.

In certain embodiments of the RNAi agents, at least one of the sense and antisense strands are modified by at least one modification selected from the group consisting of 2'-O-methyl, 2'-O-(2-methoxyethyl), 2'-F, locked nucleic acid (LNA), and phosphorothioate. In a particular example, the sense strand includes SEQ ID NO: 7.

In still other embodiments, the RNAi agent is conjugated to a cholesterol, α-tocopherol moiety, or a cell penetrating peptide.

Also provided herein are drug delivery devices (DDD), which include a biodegradable polymeric matrix; and at least one of the RNAi agents described herein, Additional RNAi agents and anti-cancer non-RNAi agents can be incorporated into the DDDs.

In particular embodiments, the described DDDs also include an additive for modulating drug-polymer hydrophobic-hydrophilic interactions, such as mannitol, trehalose, sorbitol, glucose, fructose, galactose, or sucrose.

In other embodiments, the described DDDs also include a pH-modulating additive, such as sodium bicarbonate.

In particular embodiments of the described DDDs, the biodegradable polymeric matrix is made at least in part from a poly(lactic-co-glycolic acid) (PLGA) co-polymer comprising PLA and PGA, and wherein the PLA and the PGA are present in the co-polymer in a ratio of PLA:PGA equal to or larger than 75:25, or equal to or smaller than 25:75.

In some embodiments, the DDDs further include polymeric particles, such as biodegradable polymeric particles, and which are made at least in part from a polymer different from the polymer of the DDD; and the RNAi agent that is incorporated within the DDD matrix. Further provided herein are methods for treating a cancer expressing HSP90 in a subject by administering the RNAi agent of claim 1 to the subject, thereby treating the cancer.

In particular embodiments, the methods include methods for treating a solid tumor. In such methods, the RNAi agent is provided in the context of a described DDD that is implanted into the tumor or surrounding tumor bed.

IV. RNAi Agents Inhibiting HSP90

Described herein are RNA interference (RNAi) agents for targeting and decreasing the expression of heat shock protein 90 (HSP90) in a cancerous cell, such as in the context of a solid tumor.

In particular embodiments, an RNAi agent is a short (or small) interfering RNA (siRNA), short hairpin RNA (shRNA), or microRNA. In other embodiments RNAi agents include longer polynucleotide molecules that are processed intracellularly to yield siRNA. Particular examples include DsiRNA, which are cleaved by the RNase III class endoribonuclease dicer into 21-23 base duplexes having a 2-base 3'-overhang; UsiRNAs, which are duplex siRNAs that are modified with non-nucleotide acyclic monomers, termed unlocked nucleobase analogs (UNA), in which the bond between two adjacent carbon atoms of ribose is removed, and which may be designed to enter the RNAi pathway via Dicer enzyme or directly into RISC; self-delivering RNA (sdRNA) such as rxRNA® of RXi Therapeutics, and agents inhibiting the pre-mRNA maturation step of polyA tail addition such as the U1 adaptor (Integrated DNA Technologies (IDT) Inc). Other modifications from Table 4 may be used as well.

In particular embodiments, the target of an RNAi agent described herein, such as an RNAi agent present in a DDD, is a region of the HSP90 mRNA sequence set forth as any one of SEQ ID NOs: 1-3.

In other embodiments, RNAi agent is double-stranded, such as in a siRNA, and the sense sequence of each HSP90-targeting siRNA includes any one of SEQ ID NOs: 4-6. In other embodiments wherein the RNAi agent is double-stranded, the anti-sense strand includes any one of SEQ ID NOs 8-10. It is understood that multiple HSP90-targeting RNAi agents can be used in the described compositions and methods.

Targeted HSP90 sequences and illustrative siRNA sense and anti-sense strands are presented in Tables 1-3:

TABLE 1

| HSP90 mRNA Target Sequences | | |
|---|---|---|
| Target Name | SEQ ID NO: | Sequence |
| si-HSP1-1 | 1 | 5'-AAG ACC AAC CGA UGG AGG A-3' |
| si-HSP1-2 | 2 | 5'-AAG AGC UGC AUA UUA ACC U-3' |
| si-HSP1-3 | 3 | 5'-AAG UCU GGG ACC AAA GCG U-3' |

TABLE 2

| siRNA Sense Strand Sequences | | |
|---|---|---|
| Target Name | SEQ ID NO: | Sequence |
| si-HSP1-1 | 4 | 5'-AAG ACC AAC CGA UGG AGG AdTdT-3' |

TABLE 2-continued siRNA Sense Strand Sequences

| Target Name | SEQ ID NO: | Sequence |
|---|---|---|
| si-HSP1-2 | 5 | 5'-AAG AGC UGC AUA UUA ACC UdTdT-3' |
| si-HSP1-3 | 6 | 5'-AAG UCU GGG ACC AAA GCG UdTdT-3' |

TABLE 3 siRNA Anti-sense Strand Sequences

| Target Name | SEQ ID NO: | Sequence |
|---|---|---|
| si-HSP1-1 | 8 | 5'-UCC UCC AUC GGU UGG UCU UdTdT-3 |
| si-HSP1-2 | 9 | 5'-AGG UUA AUA UGC AGC UCU UdTdT-3' |
| si-HSP1-3 | 10 | 5'-ACG CUU UGG UCC CAG ACU UdTdT-3' |

In certain embodiments, the HSP90-targeting RNAi agent is between 19-30 nucleotides (nt) in length, such as 25-27 nt and 19-25-nt. In other embodiments, the RNAi agent is 19 nt long. In other embodiments, the sense strand and/or the antisense strand further comprises a 1-6-nt 3'-overhang. In particular embodiments, the RNAi agent is 100% complementary to its target sequence. In other embodiments, the RNAi agent is only partially complementary 1, 2, 3 or more nucleotides that are different from its target sequence. In other embodiments, a two-base 3' overhang is present. In more specific embodiments, the sense strand and the antisense strand each further comprises a 2-nt 3'-overhang. In still further embodiments, the 3' overhangs are made from consecutive deoxythymine (dT) nucleotides, such that a 2 nt 3' overhang is dTdT. Examples of siRNA agents having 3' dTdT overhangs include the sense strand sequences set forth as SEQ ID Nos 4-6 and the anti-sense sequences set forth as SEQ ID NOs 8-10. In other embodiments, an siRNA used in the described methods and compositions has a 19+2 overhang design, namely sense and anti-sense of 19 base-paired nucleotides and two unpaired nucleotides at the 3' end of each of the strands. In certain embodiments, as exemplified herein, the overhangs are each dTdT.

In other embodiments, one or more nucleotides of the described HSP90-targeting RNAi agent are modified by 2'-OMe or 2'-F. In particular embodiments, such modifications are made in one or both strands of a described siRNA on one or more nucleotides. The described modified sequences may be used with or, in other embodiments without, overhangs at the 3' end of each of the strands (in the instance of a dsRNA RNAi agent). In certain embodiments, the overhangs each consist of two unpaired nucleotides. In more specific embodiments, as exemplified herein, the overhangs are each dTdT (2 deoxythymidine residues). In a particular example the siRNA has a sense strand having the sequence set forth as SEQ ID NO: 7 (5'-AAG ACCo AAC CGA UoGG AGG A dTdT-3).

In other embodiments, the described RNAi agents can be chemically modified, separate from or in addition to the modifications described above. In a particular embodiment, the modification is a backbone or linkage modification. In another embodiment, the modification is a nucleoside base modification. In a further embodiment, the modification is a sugar modification. In more specific embodiments, the modification, including the nucleotide modifications described above, is selected from the modifications appearing in Table 4 below. In other embodiments, the modification is selected from a locked nucleic acid (LNA) and/or peptide nucleic acid (PNA) backbone. Other modifications are described in US Patent Application Pub. No. 2011/0195123.

TABLE 4

RNAi agent modifications

| Modification | Position of the substitution |
|---|---|
| Sugar modifications | |
| dNTPs-dTdT | 3'-overhangs of sense and/or anti-sense strands |
| dNTPs-dNPs | Any number of residues in the sense strand; 0-4 residues at the 5' end of the antisense strand |
| 2'-O-methyl (2'OMe) rNPs | Any number of residues in the sense and/or antisense strands |
| 2'-fluoro (2'-F) rNPs | Any number of pyrimidine residues in the sense and/or antisense strands |
| combined use of 2'OMe and 2'-F | Any number of pyrimidine residues in the sense and/or antisense strands to 2'-F; and any number of purine residues in the sense and antisense strands to 2'-OMe. |
| 2'-O-(2-methoxyethyl) (MOE) rNPs | Any number of pyrimidine residues in the sense and/or antisense strands |
| 2'-fluoro-β-D (FANA) rNPs | Any number of pyrimidine residues in the sense strand |
| Locked nucleic acids (LNA) | from none till 4 last ribonucleotides at the 3' end of the sense strand; and 3' overhangs of the antisense strand |
| combined use of DNA and 2'-F | substitution of any number of pyrimidine (T and C) ribonucleotides to 2'-F ribonucleotides and any number of purines (A and G) to deoxyribonucleotides in sense and/or antisense strands |
| phosphate linkage modifications - phosphorothioate (PS) | |
| phosphodiester | substitution of any number of ribonucleotides in sense and/or antisense strands |
| phosphorothioate (PS) | substitution of any number of ribonucleotides in sense and/or antisense strands |
| boranophosphate DNA or RNA | substitution of any number of ribonucleotides in sense and/or antisense strands |
| amide-linked | substitution of any number of ribonucleotides in sense and/or antisense strands |
| phosphoramidate | substitution of any number of ribonucleotides in sense and/or antisense strands |
| methylphosphonate | substitution of any number of ribonucleotides in sense and/or antisense strands |
| 2',5'-linked DNA or RNA | substitution of any number of ribonucleotides in sense strand |
| Base modifications | |
| 5-bromouracil (5-Br-Ura) | substitution of any number of ribouraciles in sense and/or antisense strands |
| 5-iodouracil (5-I-Ura) | substitution of any number of ribouraciles in sense and/or antisense strands |
| dihydrouracil | substitution of any number of ribouraciles in sense and/or antisense strands |

TABLE 4-continued

RNAi agent modifications

| Modification | Position of the substitution |
| --- | --- |
| 2-thiouracil | substitution of any number of ribouraciles in sense and/or antisense strands |
| 4-thiouracil | substitution of any number of ribouraciles in sense and/or antisense strands |
| pseudouracil | substitution of any number of ribouraciles in sense and/or antisense strands |
| diaminopurine | substitution of any number of adenines in both sense and/or antisense strands |
| difluorotoluene | substitution of any number of adenines in both sense and/or antisense strands |
| peptide nucleic acids (PNAs) (2-aminoethylglycine) | substitution of any number of ribonucleotides in sense and/or antisense strands |
| modifications to the overhangs and termini | |
| 2-nt-3'-DNA overhang | 3' end of sense and/or antisense strands |
| 2-nt-3'-RNA overhang | 3' end of sense and/or antisense strands |
| blunt-ended duplexes | 3' end of sense and/or antisense strands |
| chemical conjugation | |
| cholesterol | covalently attached to sense and/or antisense strands |
| vitamin-E (α-tocopherol) | covalently attached to sense and/or antisense strands |

In other embodiments, the described RNAi agent may be conjugated to cholesterol, a cell penetrating peptide, or alpha-tocopherol-vitamin E. In certain embodiments wherein the RNAi agent is double-stranded, the cholesterol may be conjugated to the 3' end of the sense strand. In other embodiments, the cholesterol may be conjugated to the 5' end of the sense strand. In certain embodiments, in the case of a hairpin-shaped molecule, the cholesterol may be conjugated to the loop. These and further examples of conjugating molecules are described in US Patent Application Pub. No. 2011/0195123.

In certain embodiments, the RNAi agent is associated, either via covalent attachment or via non-covalent complexation, with a cell-penetrating peptide (CPP), also referred to as protein transduction domains (PTDs), which can facilitate the delivery of a molecular cargo to the cytoplasm of a cell. Non-limiting examples of CPP's include HIV-1 Tat (NCBI Gene ID: 155871) or a fragment thereof comprising the sequence YGRKKRRQRRR (SEQ ID No: 11); pAntp (penetratin) (NCBI Gene ID: 40835); Is1-1 (NCBI Gene ID: 3670); Transportan, Pooga et al), MPG (GALFLGFL-GAAGSTMGA [SEQ ID No: 12]; and Pep-1 (KETW-WETWWTEW; SEQ ID No: 13). CPP's are known to those skilled in the art and are described inter alia in Deshayes et al.

In other embodiments, the described RNAi agents may be complexed with a cationic molecule, such as DOTAP (N-[1-(2,3-Dioleoyloxy)propyl]-N,N,N-trimethylammonium), DOPE (1,2-dioleoyl-sn-glycero-3-phosphatidyletha-nolamine), 1,2-dioleoyl-sn-glycero-3-phosphocholine (DOPC), 1,2-di-O-octadecenyl-3-trimethylammonium propane (DOTMA), spermine, PEI (polyethylenimine), a PEI-PLA polymer, or N-Acetylgalactosamine (GalNAc).

In particular embodiments, the RNAi agents are formulated for systemic delivery, in other embodiments, the RNAi agents are formulated for local delivery to an area of treatment.

V. Drug Delivery Devices for Delivering HSP90 RNAi Agents

Further provided herein are drug delivery devices (DDDs) for sustained release of the described HSP90-targeting RNAi agents. The DDD is generally composed of a biodegradable polymeric matrix; and at least one of the HSP90-targeting RNAi agents described herein, wherein the RNAi agent is incorporated within the biodegradable polymeric matrix.

The described DDD can be a cylinder, a sphere, or any other shape suitable for an implant (i.e. that can be implanted in a subject). In particular embodiments, the DDD is of "millimeter-scale." That is, a device whose smallest diameter is a least 0.3 mm. In certain embodiments, each of the dimensions (diameter, in the case of a sphere or cylinder; and height and/or width or length, in the case of a cylinder, box-like structure, cube, or other shape with flat walls) is between 0.3-10 mm, inclusive. In other embodiments, each dimension is between 0.5-8 mm, inclusive. In still other embodiments, each dimension is between 0.8-5.2 mm, inclusive, between 1-4 mm, inclusive, between 1-3.5 mm, inclusive, between 1-3 mm, inclusive, or between 1-2.5 mm, inclusive.

In particular embodiments, the device is a cylinder, having a diameter of 0.8 mm. In other preferred embodiments, the cylinder has a length of 5 mm. In other embodiments, the cylinder has a diameter of about 0.8 mm and a length of 5 mm. In other embodiments, a DDD of the described methods and compositions has the diameter of an 18-gauge needle.

In other embodiments, the volume of the device is between 0.1 $mm^3$ and 1000 $mm^3$, between 0.2 $mm^3$ and 500 $mm^3$, between 0.5 $mm^3$ and 300 $mm^3$, between 0.8 $mm^3$ and 250 $mm^3$, between 1 $mm^3$ and 200 $mm^3$, between 2 $mm^3$ and 150 $mm^3$, between 3 $mm^3$ and 100 $mm^3$, or between 5 $mm^3$ and 50 $mm^3$.

In a particular embodiment, the DDD has a diameter of 0.8 mm and a length of 5 mm, containing 25% w/w siRNA, namely about 650 μg of siRNA.

In other embodiments, the w/w agent:polymer load ratio is between 1:3 and 1:100, such as above 1:100 (including 1:75, 1:50, and 1:25). In more preferred embodiments, the load is above 1:20. In more preferred embodiments, the load is above 1:9. In more preferred embodiments, the load can be even above 1:3.

The DDD is composed of polymers, wherein the RNA release mechanism includes both bulk erosion and diffusion; or in some embodiments, non degradable, or slowly degraded polymers are used, wherein the main release mechanism is diffusion rather than bulk erosion, so that the outer part functions as membrane, and its internal part functions as a drug reservoir, which practically is not affected by the surroundings for an extended period (for example from about a week to about a few months). Combinations of different polymers with different release mechanisms may also optionally be used. The concentration gradient at the surface is preferably constant during a significant period of the total drug releasing period, and therefore the diffusion rate is effectively constant (termed "zero mode" diffusion). The term "constant" refers to a diffusion rate that is maintained above the lower threshold of therapeutic effectiveness, but which may still optionally feature an initial burst and/or fluctuate, for example increasing and decreasing to a certain degree. In other embodiments, there is an initial burst of less than 10% of the total amount of drug, which may be considered negligible. In other embodiments, there is an initial burst of about 20% of the total amount of drug. In other embodiments, the design enables initial a strong burst of 30% or more of the total amount of drug. The diffusion rate is preferably so maintained for a prolonged period, and it can be considered constant to a certain level to optimize the therapeutically effective period, for example the effective silencing period.

In particular embodiments, the DDD releases an RNAi agent in a controlled fashion, which will vary depending on factors including but not limited to the DDD's constituent polymers, additives, and surface-to-volume ratio. For example, decreasing the surface-to-volume ratio will increase the duration of RNAi agent release time.

The DDDs described herein are designed with a particular drug-release profile. One relevant parameter is the time point at which 95% of the active agent has been released. In some embodiments, the DDD releases 95% of the active agent in vivo, for example in a human prostate, over a time period between 3-24 months inclusive, for example 3, 4, 5, 6, 8, 10, 12, 14, 16, 18, 20, 22, or 24 months and any duration in between, for example 3-12, 2-24, 2-15, or 3-10 months inclusive. Another relevant parameter is the time point at which 90% of the active agent has been released; this may be any of the aforementioned time frames.

Another relevant parameter is the percent of RNAi agent released at a given time point. For example, in some embodiments, 80-99% inclusive of the RNAi agent is released 3-months after implantation. In other embodiments, 80-99% of the active agent is released 2, 4, 6, 9, 12, or 24-months after implantation. Alternatively or in addition, in some embodiments no more than 30-50% of the RNAi agent is released from the DDD during the first 3 weeks after implantation. In certain embodiments, less than 5% of the RNAi agent is released from the DDD over a time period of 1 month starting from implantation. In other embodiments, less than 10% of the RNAi agent is released from the DDD over a time period of 1 month starting from implantation.

Delayed-release DDDs are utilized with the described RNAi agents. "Delayed-release", as used herein, refers to DDDs that do not release more than 10% of RNAi agent within the first 2 months (discounting an initial burst of up to 20%, which sometimes occurs). In other embodiments, the DDD does not release more than 10% of its drug load within the first 3 months. In particular embodiments, DDDs containing 1% trehalose exhibit delayed release.

In other embodiments, the DDD is coated (by dipping, spraying, or any other method known to those skilled in the art) with a slowly-degraded polymer that contains no drug. Various embodiments of slowly-degraded polymers are described herein, each of which can be utilized to create a delayed-release DDD. In some embodiments, the coating comprises a linear-chain monosaccharide; a disaccharide; a cyclic monosaccharide, a cyclic disaccharide. In other embodiments, the coating comprising an additive selected from lactose, sucrose, dextran, and hydroxyethyl starch. In yet other embodiments, the coating comprises mannitol. Alternatively, the coating may comprise trehalose. In still other embodiments, the coating does not comprise a sugar.

The DDD contains a biodegradable polymeric matrix into which the RNAi agent is incorporated. In particular embodiments, the matrix is composed of poly(lactic acid) (PLA). In other embodiments, the biodegradable matrix is composed of poly(glycolic acid) (PGA). In still other embodiments, the biodegradable matrix comprises the co-polymer of PLA and PGA known as poly(lactic-co-glycolic acid) (PLGA).

PLGA matrices of varying ratios PLA:PGA are well known and are commercially available. Likewise, methods for making such matrices that incorporate RNAi agents are well known in the art. Exemplary methods are described in described in US Patent Application Pub. No. 2011/0195123. In particular embodiments, the PLA:PGA ratio in the PLGA copolymer is between 95:5 and 5:95, and more particularly between 25:75 and 75:25. In other embodiments, the ratio is between 50:50 and 75:25, meaning that the amount of co-polymer in the DDD includes between 50-75% PLA and between 25-50% PGA. In other embodiments, the PLA:PGA ratio is between 25:75 and 50:50, between 35:65 and 75:25, between 45:55 and 75:25, between 55:45 and 75:25, between 65:35 and 75:25, between 75:25 and 35:65, between 75:25 and 45:55, between 75:25 and 55:45, or between 75:25 and 65:25. In other embodiments, the PLA:PGA ratio is between 80:20 and 90:10, inclusive. In other embodiments, the PLA/PGA ratio is larger than 75:25, between 75:25 and 85:15, or between 75:25 and 95:5. Alternatively, the ratio is smaller than 25:75, between 25:75 and 15:85, or between 25:75 and 5:95. In some embodiments, the co-polymer has a PLA:PGA ratio of between 80:20 and 90:10, inclusive, for example 80:20, 82:18, 84:16, 86:14, 88:12, or 90:10. In other embodiments, the co-polymer has a PLA:PGA ratio larger than 75:25, for example 76:24, 78:22, 80:20, 82:18, 84:16, 86:14, 88:12, 90:10, 92:8, 94:6, 96:4, or 98:2. In yet other embodiments, the co-polymer has a PLA:PGA ratio smaller than 25:75, inclusive, for example 24:76, 22:78, 20:80, 18:82, 16:84, or 14:86, 12:88, 10:90, 8:92, 6:94, 4:96, or 2:98.

In other embodiments the biodegradable polymeric matrix is composed of PEG (poly(ethylene glycol), which can be the majority of the DDD or used in combination with any other polymer described herein.

Other polymers that can be used in the described DDDs include tri-block PLA-PCL-PLA, wherein PCL denotes poly-caprolactone; Poly(D,L-lactide) (DL-PLA), poly(D,L-glycolide); or poly(D,L-lactide-co-glycolide). Design of biodegradable controlled drug-delivery carriers containing PLA, PGA, PEG, and/or PCL to have a specified release profile are described inter alia in Makadia and Siegel, Polymers 2011, 3:1377-1397.

In some embodiments, a polymer used in the described DDDs has a molecular weight (MW) of greater than 5 kilodaltons (kDa). In other embodiments, the MW is greater than 50 kDa. In other embodiments, the MW is greater than 7 kDa, 10 kDa, 15 kDa, 20 kDa, 30 kDa, 70 kDa, 100 kDa, 150 kDa, or greater than 200 kDa. In other embodiments, the MW is between 5-100 kDa, between 7-80 kDa, 10-60 kDa, 20-50 kDa, or between 25-50 kDa. In a particular example extended, slow release (approximately 6 months) can be achieved with a DDD containing PLGA co-polymer having a high PLA:PGA ratio, such as 90:10, and a MW (molecular weight) higher than 50 KDa. A similar effect can be achieved by use of PLA.

In other embodiments, the biodegradable matrix further comprises one or more additives for a variety of purposes including modulating hydrophilic-hydrophobic interactions; enabling dispersion of the drug, eliminating aggregation; preserving the drug in hot-temperature or cold-temperature storage conditions; and facilitating creation of cavities in the implant that affect drug diffusion from the matrix.

Hydrophilic-hydrophobic interactions may cause aggregation of the active substance in cases of hydrophilic active substances, such as siRNA, incorporated within a hydrophobic polymer, resulting in aggregation during production or subsequently when the device is implanted into the body of a subject and is subjected for example to hydrolysis. Non-limiting examples of such an additive to reduce such interactions are open monosaccharides, for example mannitol; disaccharides such as trehalose; sorbitol; and other cyclic monosaccharides such as glucose, fructose, galactose and disaccharides such as sucrose. The above additives, when chiral, can be in the form of the D-enantiomer, the L-enantiomer, or a racemic mixture. Additional, non-limiting examples of such additives are lactose, sucrose, dextran, and hydroxyethyl starch.

In particular embodiments, the DDD has between 1% and 15% mannitol, such as 1%, 1.5%, 2%, 2.5%, 5%, 7.5%, 10%, or 12.5%, and 15%, or any amount between.

In other particular embodiments, the DDD has less than 5% trehalose, for example in different embodiments 0.5%, 1%, 1.5%, 2%, 2.5%, 3%, 3.5%, 4%, or 4.5%, the effects of which on RNAi agent release can be readily tested.

In other embodiments, the biodegradable matrix comprises an additive for protecting the RNAi agent against low pH after implantation. The microenvironment in the DDD implant interior tends to be acidic. Unlike chemotherapy, pH should preferably be maintained above a threshold. For example, RNAi drugs might degrade at pH<3. In more specific embodiments, such a pH modulating (i.e. pH-changing) additive may be selected from bicarbonates and carbonates, for example sodium bicarbonate, sodium carbonate, and magnesium hydroxide. In particular examples, sodium bicarbonate is included at a concentration between 0.05% to about 5%, such as about 1%. In other examples, sodium bicarbonate (or other pH modulating agent) is included at less than 1%, including 0.9%, 0.8%, 0.7%, 0.6%, 0.4%, and 0.2% or even less. In still other examples, sodium bicarbonate (or other pH modulating agent) is included at 2%, 3%, 4%, 5%, or any increment in between 1% and 5%.

In particular embodiments, in addition to the RNAi agent described herein, other anti-cancer therapeutic agents can be incorporated into and delivered by the described DDDs. Non-limiting examples of such agents include RNAi agents targeting other cancer-associated genes; small molecule chemotherapeutic agents, and other biologic immunotherapeutic agents such as but not limited to immunomodulating cytokines and monoclonal antibodies. Examples of RNAi agents that target a non-HSP90 gene are described extensively in, inter alia, United States Patent Publication 2014/0314854, nd U.S. Pat. No. 9,006,199, and International Patent Application PCT/IL2013/050944; the contents of all of which are incorporated by reference in their entirety.

The described DDDs can contain at least 10 μg of an RNAi agent, such as a siRNA. In other embodiments, the amount is between 10-2000 μg siRNA per device. including between 300-1700 μg siRNA per device, between 300-1100 μg siRNA per device, or between 400-900 μg siRNA per device.

It is appreciated that multiple DDDs can be implanted in a given treatment. The amount of the RNAi agent in all the DDD's administered as a batch (a single dose) can be at least 4 μg, for example at least 5 μg, at least 6 μg, at least 7 μg, at least 8 μg, at least 10 μg, at least 12 μg, or at least 15 μg. In still other embodiments, the amount of RNAi agent present per dose is between 2-10 μg, inclusive, for example 2, 3, 4, 5, 6, 7, 8, 9, or 10 μg In yet other embodiments, all the DDD's administered as a batch deliver a dose of 0.008-0.065 mg/kg/month, inclusive, for example 0.008 mg/kg/month, 0.01 mg/kg/month, 0.015 mg/kg/month, 0.02 mg/kg/month, 0.03 mg/kg/month, 0.05 mg/kg/month, or 0.065 mg/kg/month.

In certain embodiments, the drug percentage of the described DDDs is at least 20%. In another embodiment, the drug percentage is at least 30%, for example 30%, 35%, 40%, 45%, 50%, 55%, or 60%. In another embodiment, the drug percentage is between 8-30%, inclusive, for example 8%, 9%, 10%, 11%, 12%, 13%, 14%, 15%, 16%, 17%, 18%, 19%, 20%, 22%, 24%, 26%, 28%, or 30%.

As described, a large variety of DDDs can be contemplated, taking the various amounts of polymer, RNAi agent and optional additives. Particular non-limiting examples of such DDDs follow.

In a particular embodiment, the DDD contains 64-76% PLGA (with a ratio of PLA:PGA at 90:10); 16-27% RNAi agent; and 5-12% mannitol, with or without 0.05%-1.5% sodium bicarbonate.

In still other embodiments, the described DDD contains trehalose and not mannitol. In still other embodiments, the DDD comprises both trehalose and mannitol. In more specific embodiments, the DDD may contain 70-91.2% PLGA; 8-30% siRNA; 0.6-1.5% trehalose; and 0.1-0.4% sodium bicarbonate. In other embodiments, the DDD may contain 75-91.2% PLGA; 8-25% siRNA; 0.6-1.5% trehalose; and 0.1-0.4% sodium bicarbonate. In still other embodiments, the DDD may contain 80-91.2% PLGA; 8-20% siRNA; 0.6-1.5% trehalose; and 0.1-0.4% sodium bicarbonate. In yet other embodiments, the DDD may contain 85-91.2% PLGA; 8-15% siRNA; 0.6-1.5% trehalose; and 0.1-0.4% sodium bicarbonate. In additional embodiments, the DDD may contain 88-91.2% PLGA; 8-12% siRNA; 0.6-1.5% trehalose; and 0.1-0.4% sodium bicarbonate. In yet other embodiments, the DDD may contain 89-91% PLGA; 8-10% siRNA; 0.6-1.5% trehalose; and 0.1-0.4% sodium bicarbonate. In still other embodiments, the DDD may contain about 90% PLGA 85:15, about 9% siG12D, about 1% Trehalose, and about 0.2% NaHCO$_3$.

In other embodiments, the described DDDs can be coated. A coating can be designed for a number of characteristics, including modulating the release rate or preventing protein stickiness during long-term storage. The coating in some embodiments comprises the same material used to form the matrix, for example a PLGA co-polymer matrix, but without the RNAi agent. In other embodiments, the coating comprises a material similar to that used to form the matrix (for example containing the same building blocks in a different ratio, or containing the same polymer but with a different MW), only without the RNAi agent. In other embodiments, the coating comprises the same material used to form the matrix, together with at least one other polymeric material such as PEG. In other embodiments, the coating includes PLA. In still other embodiments, the coating includes a PLGA co-polymer wherein the PLA:PGA are in a ratio of at least 80:20, for example 80:20, 82:18, 84:16, 85:15, 86:14, 88:12, 90:10, 92:8, 94:6, 96:4, 98:2, and 99:1, and having a MW greater than 50 KDa, for example 60 KDa, 70 KDa, 80 KDa, 100 KDa, 120 KDa, 1500 KDa, or 200 KDa).

In particular embodiments, the described DDDs also contain RNAi-agent-complexed small particles, which are distributed within the biodegradable polymeric matrix of the DDD. Small particles include "microparticles" and "nanoparticles," Microparticles include particles having a size within the range 800 nm-5 μm (also referred to as microspheres). Nanoparticles include particles of size within the range 4 nm-800 nm. (The lower size of ~4 nm typifies the smaller particles described here, which in typical embodiments is not a sphere, but a molecular complex, for example a drug molecule such as an siRNA molecule that is complexed with a polymer or conjugated to an additional molecule(s)).

In certain embodiments, the particles comprise a polymeric material as described herein, which can be different from or identical to that in the matrix.

"Different from" refers to a polymer made from different building blocks from that in the matrix or even sharing at least one building block with the polymer in the matrix, but having a different composition. For example, the particles can be composed of PLA, whereas the surrounding matrix of the DDD can be composed of PLGA. In another example the differences between the polymers in the particles and the DDD matrix include polymers containing a particular enantiomer as opposed to a racemic mixture of a given building block (L-PLA vs. DL-PLA), polymers containing the same building blocks in a different ratio (having either the same or different molecular weight (MW), or containing the same building blocks but having a different MW (having either the same or different ratio. "Identical to" refers to polymers with the same building blocks, in the same ratio, and with the same MW.

It will be appreciated that particles composed of polymers that are "identical to" the constituent polymer of the DDD matrix can contain additional materials that are different from the matrix. In particular embodiments, the polymer in the particles is non-identical to the polymer in the matrix.

In still other embodiments, the small particles do not comprise a polymeric-matrix. For example, the particles may be liposomes. Other examples include particles comprising DOTAP or PEI, or another cationic molecule complexed with the RNAi agent, as similarly described above.

In particular embodiments of DDDs that include RNAi-complexed small particles, particle complexes, for example siRNA-DOTAP complexes, are dissolved in chloroform and incorporated within larger PLA particles. Such particles are then suspended in ethyl acetate and mixed with PLGA to form a matrix.

In particular examples both the DDD matrix and the small particles are complexed with the RNAi agent. In other examples, the DDD matrix is not complexed with the RNAi agent, but the suspended particles are complexed with the RNAi agent. In those embodiments wherein both the DDD matrix and the particles are complexed with the RNAi agent, the RNAi agent can be the same in the matrix and particles or different in the matrix and particles.

Additional examples of DDDs containing small particles, including constituent components, methods of production and the like, can be found in US Patent Publication No. 2013/0122096, the contents of which are incorporated by reference herein in their entirety.

VI. Methods of Treatment

Also provided herein are methods of treatment of a cancer expressing HSP90 in a subject by administering the described RNAi agent to the subject. Such methods include treatment of a solid tumor, in which the tumor's constituent cells express HSP90, the methods including implanting a described DDD into the tumor or surrounding tumor bed.

As described herein, HSP90 is known to be involved in the post translational processing of many cancer-related proteins. Accordingly, the described ability to reduce the expression of HSP90 in a given target cell will decrease cancer cell stimulation and maintenance factors and allow for treatment of multiple cancer types, all of which are dependent on HSP90 expression.

In particular embodiments, the cancer is a prostate carcinoma. In other nonlimiting embodiments, the cancer is another cancer such as a cancer selected from a pancreatic tumor, a colon tumor, a lung tumor, brain cancer, liver cancer, kidney cancer, melanoma, endometrial carcinoma, gastric carcinoma, renal carcinoma, biliary carcinoma, cervical carcinoma, and bladder carcinoma. In more specific embodiments, the cancer is selected from pancreatic carcinoma, pancreatic ductal adenocarcinoma, small-cell lung carcinoma, and colorectal cancer.

In particular embodiments, a mixture of delayed release and non-delayed release DDDs are implanted into the subjected. Provision of a combination of delayed-release and non-delayed-release DDD's in some embodiments enables a longer time course of significant siRNA release, without the need for repeated therapeutic intervention.

DDD's contains a mix of one or more of RNAi agents or mix of RNAi and non-RNAi agents. In a particular embodiment a mix of different DDDs containing different treatment agents may be used. The non-RNAi agents include, but are not limited to one or more of the chemotherapeutic agents described herein.

In particular embodiments, the HSP90-RNAi agent is administered systemically in a pharmaceutical composition and can therefore treat cancers of non-solid tumors. Such compositions comprise pharmaceutically acceptable salts and excipients that are well known in the art. In other embodiments the HSP90-RNAi agent is administered locally, including in the context of the described DDDs, and can treat solid tumors.

In some embodiments, a described DDD is implanted intratumorally. In other embodiments, the DDD is implanted into the vicinity of the tumor. In more specific embodiments, in the case of a well-defined solid tumor, several devices are spaced within the tumor volume. In yet other embodiments, several devices are implanted along a needle cavity within the tumor. In still other embodiments, the device or devices are implanted such that they are not in a direct contact with the perimeter of the tumor. Alternatively, in the case of a poorly defined solid tumor, the device is inserted into an area believed to contain tumor cells.

In still other embodiments, the methods of treatment include co-treatment with at least one additional anti-cancer agent. In more specific embodiments, the anti-cancer agent comprises a pyrimidine analogue, non-limiting examples of which are 5-azacytidine, 5-aza-2'-deoxycytidine, 5-fluorouracil, 5-fluoro-deoxyuridine (floxuridine), and 5-fluorodeoxyuridine monophosphate. In more specific embodiments, the anti-cancer agent is an inhibitor of ribonucleoside-diphosphatereductase large subunit (EC 1.17.4.1), non-limiting examples of which are motexafin gadolinium (CHEBI: 50161); hydroxyurea; gemcitabine (2',2'-difluorodeoxycytidine); elacytarabine (CP-4055; an ara-C-5'elaidic-acid-ester) and CP-4126, (CO 1.01; a gemcitabine-5'elaidic-acid-ester; Adema A D et al, *Metabolism and accumulation of the lipophilic deoxynucleoside analogs elacytarabine and CP*-4126. Invest New Drugs. 2011 Oct. 15. [Epub ahead of print]), and those described in WO2011062503, the contents of which are incorporated herein by reference. In even more specific embodiments, the anti-cancer agent comprises gemcitabine. In alternative embodiments, the anti-cancer agent is gemcitabine. In yet other embodiments, the anti-cancer agent is an EGFR tyrosine kinase inhibitor. In yet other embodiments, the anti-cancer agent comprises a thymidylate synthase inhibitor. In more specific embodiments, the anti-cancer agent comprises leucovorin (Folinic acid; 2-[[4-[(2-amino-5-formyl-4-oxo-1,6,7,8-tetrahydropteridin-6-yl)

methylamino]benzoyl] amino]pentanedioic acid). In yet other embodiments, the anti-cancer agent comprises irinotecan. In yet other embodiments, the anti-cancer agent comprises oxaliplatin. In still other embodiments, the anti-cancer agent comprises FOLFIRIN (5-fluorouracil, leucovorin, and irinotecan in combination). In still other embodiments, the anti-cancer agent is FOLFIRINOX (5-fluorouracil, leucovorin, irinotecan, and oxaliplatin in combination), or any combination of a subset of the four agents in FOLFIRINOX. In one embodiments the agent is Modified FOLFIRINOX, administrated as follows: Oxaliplatin (85 mg/m$^2$)—IV for 2 hours, immediately followed by Irinotecan (180 mg/m$^2$)—IV for 90 min. Leucovorin—400 mg/m$^2$, followed by a Fluorouracil continuous IV infusion of 2,400 mg/m$^2$ (over 46 hours) every two weeks. In yet other embodiments, the anti-cancer agent comprises an EGFR tyrosine kinase inhibitor. In more specific embodiments, the anti-cancer agent is Erlotinib. In particular embodiments, the RNAi agent is administered concurrently, prior to, or following administration of an anti-cancer agent.

In still other embodiments, the described methods include administering radiation therapy to the patient. In some embodiments, the radiation is administered to the patient after administration of the DDD, such as up to 10 days after administration of the DDD. Alternatively, the radiation is administered to the patient simultaneously with administration of the DDD. In still other embodiments, the radiation is administered to the patient before administration of the DDD. In yet other embodiments, the DDD is administered during ongoing administration of the radiation.

In particular embodiments, an RNAi agent targeting a single HSP90 sequence is administered to the subject. In other embodiments, multiple HSP90-targeting sequences are provided.

The following examples are provided to illustrate certain particular features and/or embodiments. These examples should not be construed to limit the disclosure to the particular features or embodiments described.

EXAMPLES

Example 1: In Vitro HSP-90 Targeting by siRNA

This example shows the effects of transfected siRNA targeting HSP90 in cultured prostate cancer cells.

Prostate cancer cell line LNCaP (ATCC # CRL-1740) was grown in Roswell Park Memorial Institute medium (RPMI) supplemented with 10% fetal bovine serum (FBS) and 100 units/ml penicillin/streptomycin, according to the ATCC protocol. Cells were seeded into 96-well culture plates and incubated overnight before transfection with siRNAs targeting HSP90 sequences.

Cells were transfected using Lipofectamine® 2000 transfection reagent (Life Technologies) based on manufacturer's protocol, with siRNA targeting HSP90: HSP1-1 (sense strand SEQ ID NO: 4, anti-sense strand SEQ ID NO: 8), HSP1-2 (sense strand SEQ ID NO: 5, anti-sense strand SEQ ID NO: 9), and HSP1-3 (sense strand SEQ ID NO: 6, anti-sense strand SEQ ID NO: 10). Cells were also treated with HSP90 inhibitor NVP-AUY922 (or AUY922), a resorcinylicisoxazole amide was used at 5 nM and 10 nM (with similar effect), or left untreated. After 72 hours incubation, cellular viability was determined by standard methylene blue (MB) assay, and quantitated as percentage of viable cells in relation to the untreated sample (FIG. 1). As shown in FIG. 1, LNCaP cells transfected with the particular HSP90 siRNAs had a statistically significant decrease in viability ($p<0.001$, HSP1-1 and HSP1-2; $p<0.05$, HSP1-3).

Figure 2:
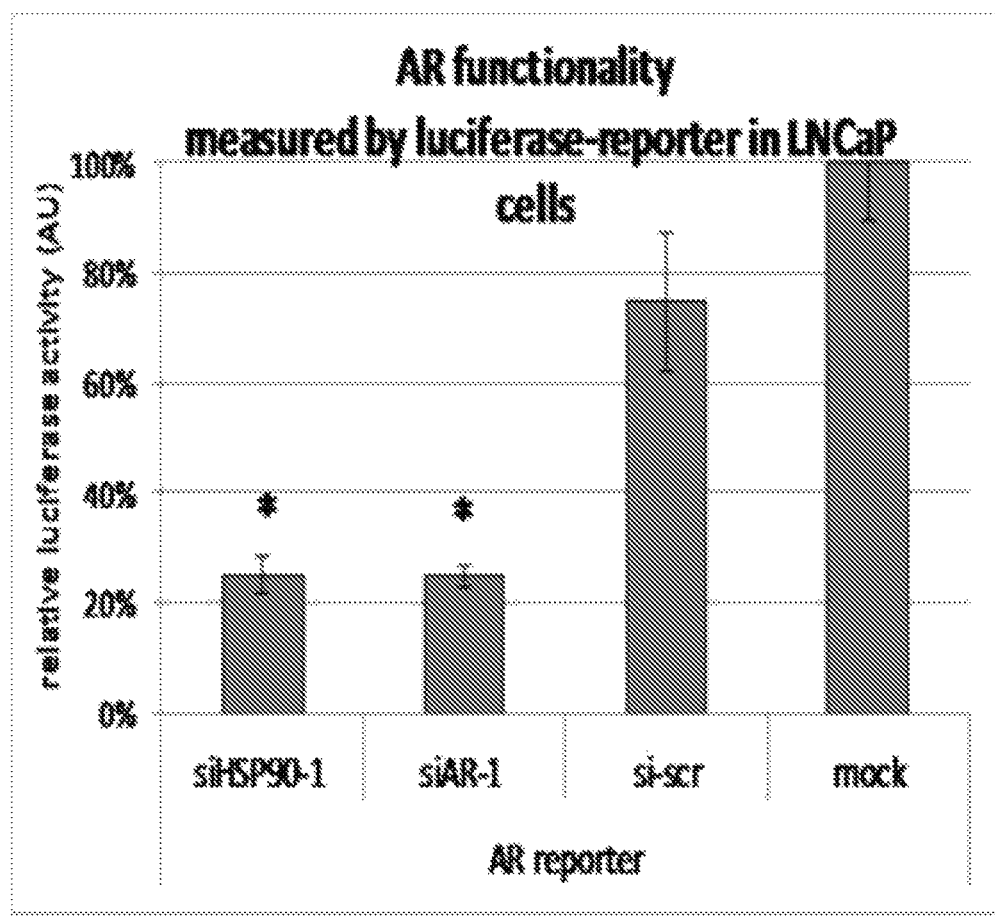
FIG. 2 shows the in vitro effect of transfected siRNAs targeting HSP90 on Androgen receptor functionality in LNCaP prostate cells Results shown are luciferase activity of an Androgen receptor luciferase reporter plasmid in transfected cells, in comparison to mock transfected cells. * indicates p<0.05

HPS90 is known to be a chaperone of AR (androgen receptor), and is necessary for correct AR post-translational processing. To further test RNAi targeting of HSP90, an AR-dependent luciferase reporter construct was used (FIG. 2). LNCaP cells were cultured as above, and were seeded onto a 48-well culture plate. After an overnight incubation, plated cells were co-transfected using Lipofectamine® 2000 transfection reagent (Life Technologies) based on manufacturer's protocol for DNA-RNA transfections with an AR-luciferase reporter plasmid (Qiagen, CCS-1019L), and siRNA targeting HSP90 (HSP1-1 (sense strand SEQ ID NO: 4, anti-sense strand SEQ ID NO: 8); AR (siAR-1), or a non-target scrambled siRNA (si-scr). Cells transfected only with the AR-luciferase reported plasmid served as the negative control (mock). 24 hours post-transfection, cells were lysed and luciferase activity determined with the Promega luciferase detection kit. Similar to the cell viability results, luciferase activity was significantly decreased in cells transfected with siRNA targeting HSP90 ($p<0.05$). This indicates that HSP90 targeting was sufficient to decrease HSP90 chaperone function, and by extension reduce the amount of properly folded AR available for the AR-luciferase plasmid.

Example 2: In Vivo HSP-90 Targeting by siRNA Induces Tumor Necrosis and Inhibits Cancer Cell Division This example demonstrates that sustained in vivo delivery of HSP-90 siRNA can induce solid tumor necrosis and inhibit cell division within the tumor.

LNCaP cells were cultured as in Example 1. *Mycoplasma* tests was performed after cell defrost and prior to cell injection to assure that the cell line is *mycoplasma* free.

Male, SCIDbg, 8-10 week old mice were purchased from Harlan, Israel, and were housed in the Hebrew University Animal House at Hadassah Ein Kerem campus. The temperature and relative humidity controls are maintained within the range of 20 to 24° C. and 40-70% respectively. Artificial lighting will be controlled to give a cycle of 12 hours continues light and 12 hours continues dark per 24 hours. The animal experiments were approved by the institutional animal ethical approval committee.

Tumor xenografts were established by subcutaneous injection of log-phase growth viable cells, 10×10$^6$ of LNCaP cells in 504 PBS diluted 1:1 with Matrigel (Bactlab(Falcon); Matrigel Matrix; FAL354234). The cells were injected into the right flanks of the mice. Tumor growth was followed by caliper measurements. Once the tumors reach a size of ~1 cm$^3$, the donor mice were sacrificed, and the tumor removed into HBSS in a sterile tissue plate (10 cm).

Figure 3A:
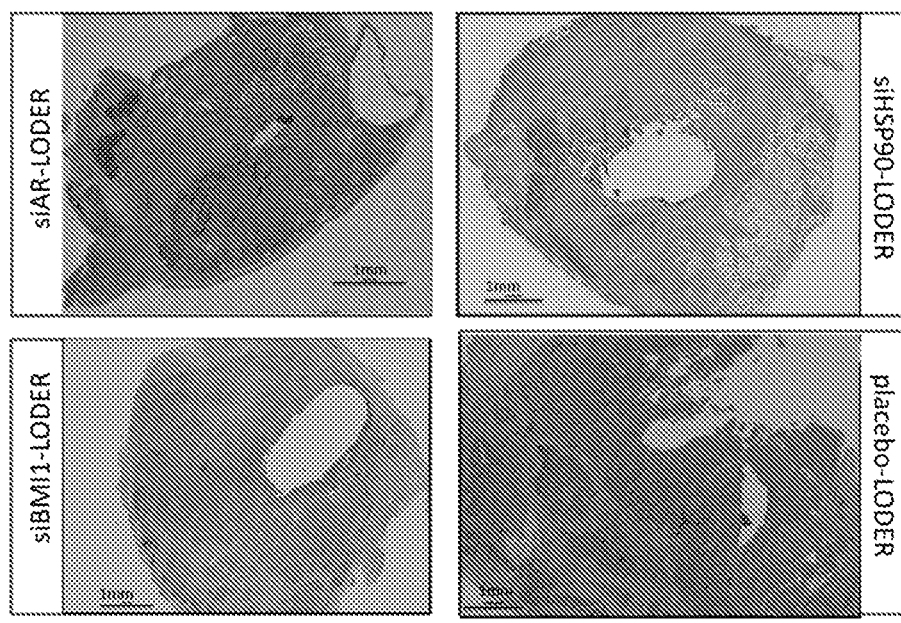
FIG. 3A are cross sections of LNCaP tumors following in vivo treatment with siRNA targeting the indicated gene and delivered by LODER (Local Drug EluteR). Shown are 5 μm sections of formalin fixed paraffin embedded tumors.
Figure 3B:
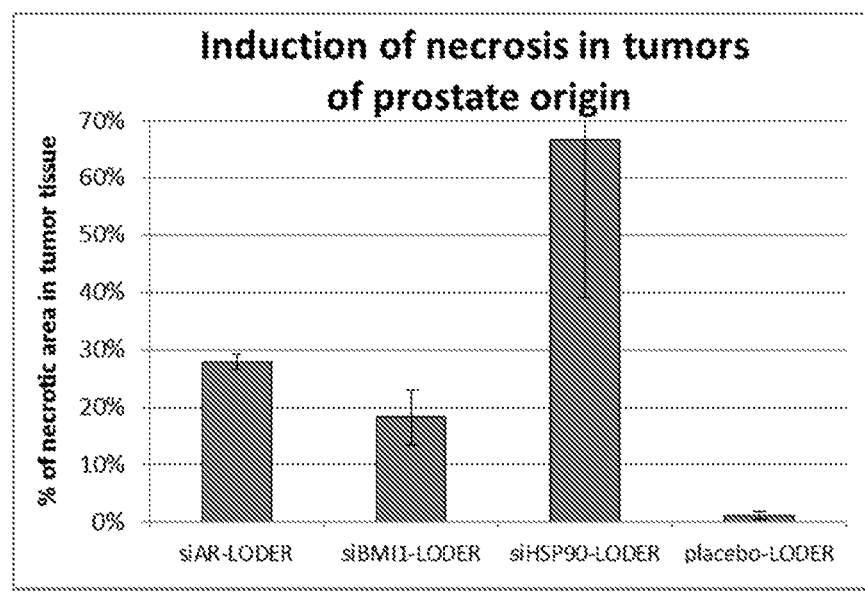
FIG. 3B is a quantitation of necrotic tissue in tumors treated as described in FIG. 3A. As presented, n=at least 3 independent mice (tumors).
Figure 4:
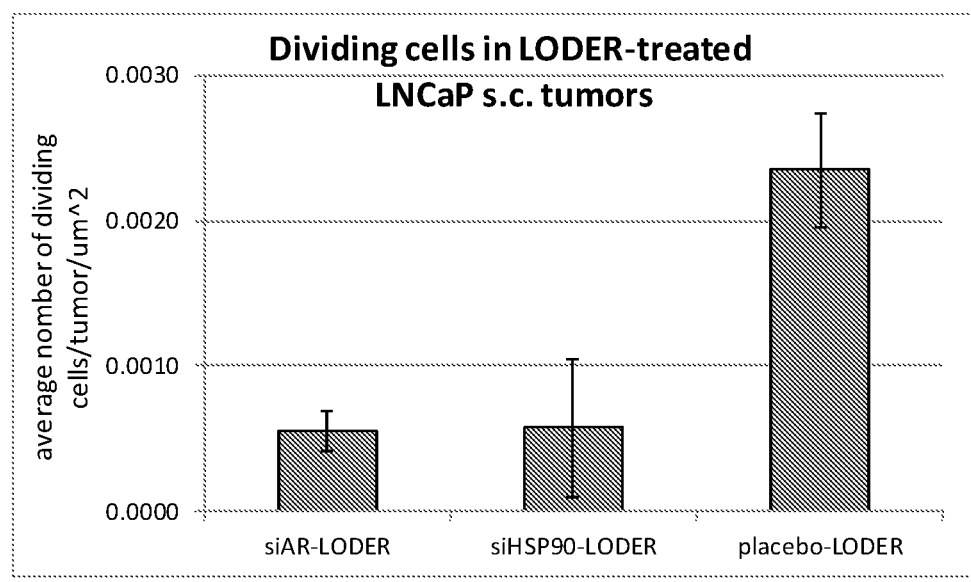
FIG. 4 shows the quantitation of dividing cells in LODER-treated LNCaP tumors. Tumors were treated and stained as shown in FIG. 3A. Mean number of dividing cells/tumor/μm are shown. As presented, n=at least 3 independent mice (tumors).

Tumors were cut into length slices and then into width slices. Tumor slices were divided into treatment groups (empty, si-HSP90, si-BMI1 and si-AR), LODERs carrying the siRNA for the indicated target were implanted into the designated slice. LODERs were comprised of PLGA, mannitol, sodium bicarbonate, and contained 5 μg of noted siRNA. The HSP90 targeting LODER carried HSP1-1 targeting RNAs as in Example 1. LODER-implanted tumor slices were pre-treated with Matrigel. The tumor slices were then implanted subcutaneously into mice following standard protocols. One week after, implantation mice were sacrificed, tumors were FFPE (formalin fixed paraffin embedded), and tissue sections of 5 μm were cut. Dividing cells were detected by CDC47 staining. Staining results reveal that in tissues treated with siAR, siBMI1 and siHSP90-LODERs the amount of necrotic tissue was significantly higher (FIGS. 3A and 3B), while the amount of dividing cells was significantly lower, compared to placebo-LODER-treated tumor tissues. Count of dividing cells reveal that siAR and siHSP90-LODERs led to inhibition in tumor cell proliferation (FIG. 4).

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. An RNAi (RNA interference) agent for treating a patient having a cancer in which cells of the cancer are expressing heat shock protein 90 (HSP90), the RNAi agent comprising a double-stranded RNA molecule that targets a HSP90 sequence set forth as SEQ ID NO: 1, or a double-stranded RNA molecule that targets a HSP90 sequence set forth as SEQ ID NO: 2, wherein the RNAi agent that targets SEQ ID NO: 1 comprises a sense strand of SEQ ID NO: 4 and an antisense strand of SEQ ID NO: 8, and wherein the RNAi agent that targets SEQ ID NO: 2 comprises a sense strand of SEQ ID NO: 5 and an antisense strand of SEQ ID NO: 9.

2. The RNAi agent of claim 1, wherein at least one of the sense and antisense strands is modified by at least one modification selected from the group consisting of 2'-O-methyl, 2'-O-(2-methoxyethyl), 2'-F, locked nucleic acid (LNA), and phosphorothioate.

3. The RNAi agent of claim 2, wherein the sense strand of the RNAi agent that targets SEQ ID NO: 1 is 2'-O-methyl-modified, and comprises SEQ ID NO: 7.

4. The RNAi agent of claim 1, wherein the RNAi agent is conjugated to a cholesterol, α-tocopherol moiety, or a cell penetrating peptide.

5. A method for treating a cancer expressing HSP90 in a subject, comprising:
  administering the RNAi agent of claim 1 to the subject, thereby treating the cancer.

* * * * *

SEQUENCE LISTING

```
<160> NUMBER OF SEQ ID NOS: 13

<210> SEQ ID NO 1
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 1
aagaccaacc gauggagga                                                   19

<210> SEQ ID NO 2
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 2
aagagcugca uauuaaccu                                                   19

<210> SEQ ID NO 3
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 3
aagucuggga ccaaagcgu                                                   19

<210> SEQ ID NO 4
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 4
aagaccaacc gauggaggat t                                                21

<210> SEQ ID NO 5
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(19)
<223> OTHER INFORMATION: RNA
<220> FEATURE:
```

```
<221> NAME/KEY: misc_feature
<222> LOCATION: (20)..(21)
<223> OTHER INFORMATION: DNA

<400> SEQUENCE: 5
aagagcugca uauuaaccut t                                              21

<210> SEQ ID NO 6
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 6
aagucuggga ccaaagcgut t                                              21

<210> SEQ ID NO 7
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (6)..(6)
<223> OTHER INFORMATION: 2'-O-methyl modified residue
<220> FEATURE:
<221> NAME/KEY: misc_feature
<222> LOCATION: (13)..(13)
<223> OTHER INFORMATION: 2'-O-methyl modified residue
<220> FEATURE:
<221> NAME/KEY: misc_feature
<222> LOCATION: (20)..(21)
<223> OTHER INFORMATION: DNA

<400> SEQUENCE: 7
aagaccaacc gauggaggat t                                              21

<210> SEQ ID NO 8
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 8
uccuccaucg guuggucuut t                                              21

<210> SEQ ID NO 9
<211> LENGTH: 21
```

```
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 9
agguuaauau gcagcucuut t                                              21

<210> SEQ ID NO 10
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 10
acgcuuuggu cccagacuut t                                              21

<210> SEQ ID NO 11
<211> LENGTH: 11
<212> TYPE: PRT
<213> ORGANISM: Artificial Sequence
<220> FEATURE:
<223> OTHER INFORMATION: Synthetic peptide

<400> SEQUENCE: 11

Tyr Gly Arg Lys Lys Arg Arg Gln Arg Arg Arg
1               5                   10

<210> SEQ ID NO 12
<211> LENGTH: 17
<212> TYPE: PRT
<213> ORGANISM: Artificial Sequence
<220> FEATURE:
<223> OTHER INFORMATION: Synthetic peptide

<400> SEQUENCE: 12

Gly Ala Leu Phe Leu Gly Phe Leu Gly Ala Ala Gly Ser Thr Met Gly
1               5                   10                  15

Ala

<210> SEQ ID NO 13
<211> LENGTH: 12
<212> TYPE: PRT
<213> ORGANISM: Artificial Sequence
<220> FEATURE:
<223> OTHER INFORMATION: Synthetic peptide

<400> SEQUENCE: 13

Lys Glu Thr Trp Trp Glu Thr Trp Trp Thr Glu Trp
1               5                   10
```